(12) United States Patent
Kirk et al.

(10) Patent No.: US 11,850,444 B2
(45) Date of Patent: Dec. 26, 2023

(54) MEDICAL APPARATUS AND METHOD

(71) Applicant: Polyphotonix Limited, Sedgefield (GB)

(72) Inventors: Richard Anthony Kirk, London (GB); Martin Neil Holland, Maidenhead (GB); Thomas Snell, Stockton-on-Tees (GB); Duncan Hill, Durham (GB); Luke Stuart Barclay, Gateshead (GB)

(73) Assignee: Polyphotonix Limited, Sedgefield (GB)

( * ) Notice: Subject to any disclaimer, the term of this patent is extended or adjusted under 35 U.S.C. 154(b) by 132 days.

(21) Appl. No.: 16/893,247

(22) Filed: Jun. 4, 2020

(65) Prior Publication Data
US 2020/0384286 A1 Dec. 10, 2020

Related U.S. Application Data

(63) Continuation of application No. 14/380,255, filed as application No. PCT/GB2013/050254 on Feb. 4, 2013, now abandoned.

(30) Foreign Application Priority Data

Feb. 22, 2012 (GB) ..................................... 1203005

(51) Int. Cl.
  *A61N 5/06* (2006.01)
  *A61F 9/02* (2006.01)
  *A61F 9/04* (2006.01)
(52) U.S. Cl.
  CPC ............ *A61N 5/0613* (2013.01); *A61F 9/029* (2013.01); *A61F 9/04* (2013.01); *A61N 5/0618* (2013.01);
  (Continued)
(58) Field of Classification Search
  CPC ............................ A61N 5/06–2005/073; A61F 9/008–2209/00897; A61B 18/20–18/28
  See application file for complete search history.

(56) References Cited

U.S. PATENT DOCUMENTS 5,585,871 A * 12/1996 Linden .................. G02C 11/00
                                                                351/158
5,634,939 A    6/1997 Kuster et al.
(Continued)

FOREIGN PATENT DOCUMENTS

CN        1787776 A    6/2006
EP        2817065 B1   4/2017
(Continued)

OTHER PUBLICATIONS

Espacenet English translation of Oshiro JP 2004313213 A (Year: 2004).*

(Continued)

*Primary Examiner* — Jonathan T Kuo
(74) *Attorney, Agent, or Firm* — Klarquist Sparkman, LLP

(57) ABSTRACT

A medical apparatus and method of operating a medical apparatus are disclosed. The apparatus includes a radiation source for emitting radiation towards an area to be treated of a patient; a mount element arranged to be worn by the patient for positioning the radiation source in a predetermined position relative to the area to be treated; a sensor element arranged to provide a signal indicative of whether the apparatus is being worn by the patient; and at least one controller arranged to receive the signal from the sensor, and to determine whether the apparatus is being worn by the patient, and to determine duration data indicative of the duration for which the radiation source emits radiation whilst the apparatus is being worn by the patient.

17 Claims, 8 Drawing Sheets

(52) U.S. Cl.
CPC ................. *A61N 2005/0626* (2013.01); *A61N 2005/0648* (2013.01); *A61N 2005/0653* (2013.01); *A61N 2005/0662* (2013.01)

(56) References Cited

U.S. PATENT DOCUMENTS

| | | | |
|---|---|---|---|
| 6,926,667 | B2 | 8/2005 | Khouri |
| 2004/0162549 | A1 | 8/2004 | Altshuler |
| 2007/0198004 | A1 | 8/2007 | Altshuler et al. |
| 2008/0062338 | A1* | 3/2008 | Herzog ............. G02F 1/133553 349/13 |
| 2008/0097548 | A1 | 4/2008 | Greenberg et al. |
| 2008/0125834 | A1 | 5/2008 | Hendrix et al. |
| 2008/0269849 | A1* | 10/2008 | Lewis .................. A61N 5/0613 607/91 |
| 2009/0018622 | A1* | 1/2009 | Asvadi ................... A42B 1/244 607/91 |
| 2010/0121419 | A1 | 5/2010 | Douglas |
| 2012/0056847 | A1 | 3/2012 | Milford |
| 2012/0215291 | A1* | 8/2012 | Pugh ..................... A61M 21/02 607/93 |
| 2014/0063055 | A1* | 3/2014 | Osterhout ............. G06T 19/006 345/633 |

FOREIGN PATENT DOCUMENTS

| | | |
|---|---|---|
| JP | S63-9453 | 1/1988 |
| JP | 2002-197200 A | 7/2002 |
| JP | 2004-313213 A | 11/2004 |
| JP | 2004313213 A * | 11/2004 |
| JP | 2008-539808 A | 11/2008 |
| WO | WO2006/099413 A2 | 9/2006 |
| WO | WO2009/059270 A1 | 5/2009 |
| WO | WO2010/076709 A1 | 7/2010 |
| WO | WO2011/135362 A1 | 11/2011 |
| WO | WO2012/054863 A1 | 4/2012 |

OTHER PUBLICATIONS

International Search Report and Written Opinion of the International Searching Authority, dated May 8, 2013, for corresponding International Application No. PCT/GB2013/050254, 12 pages.
International Preliminary Report on Patentability and Written Opinion of the International Searching Authority, dated Sep. 4, 2014, for corresponding International Application No. PCT/GB2013/050254, 8 pages.
First Office Action and Search Report from Patent Office of the People's Republic of China, for Chinese Patent Application No. 201380021123.7, dated Jan. 12, 2016.
Office Action from the United States Patent & Trademark Office in co-pending U.S. Appl. No. 14/380,255, dated Mar. 23, 2016.
Office Action from the United States Patent & Trademark Office in co-pending U.S. Appl. No. 14/380,255, dated Aug. 10, 2016.
Office Action from the United States Patent & Trademark Office in co-pending U.S. Appl. No. 14/380,255, dated Sep. 6, 2016.
Office Action (including English translation) from the Japan Patent Office, for Japanese Patent Application No. 2014-5581966, dated Oct. 18, 2016, 7 pages.
Office Action (including English translation) from the Japan Patent Office, for Japanese Patent Application No. 2014-5581966, dated Aug. 1, 2017, 6 pages.
Second Office Action and Search Report from State Intellectual Property Office of People's Republic of China, for Chinese Patent Application No. 201380021123.7, dated Nov. 8, 2016, 16 pages.
Office Action from the United States Patent & Trademark Office in co-pending U.S. Appl. No. 14/380,255, dated Mar. 24, 2017.
Third Office Action and Search Report from State Intellectual Property Office of People's Republic of China, for Chinese Patent Application No. 201380021123.7, dated Apr. 17, 2017, 14 pages.
Office Action from the United States Patent & Trademark Office in co-pending U.S. Appl. No. 14/380,255, dated Sep. 5, 2017.
Office Action from the United States Patent & Trademark Office in co-pending U.S. Appl. No. 14/380,255, dated Jun. 11, 2018.
Dismissal of the Appeal in Japanese Patent Application No. 10-2014-558196, Dec. 25, 2018, 19 pages.
Office Action from the United States Patent & Trademark Office in co-pending U.S. Appl. No. 14/380,255, dated Jan. 18, 2019.
Notice of Preliminary Rejection in Korean Patent Application No. 10-2014-7026308 (with English Translation), dated Jan. 22, 2019, 13 pages.
Office Action from the United States Patent & Trademark Office in co-pending U.S. Appl. No. 14/380,255, dated May 31, 2019.
Office Action from the United States Patent & Trademark Office in co-pending U.S. Appl. No. 14/380,255, dated Dec. 5, 2019.
Search Report from Great Britain Intellectual Property Office, for Patent Application No. GB1203005.2, dated May 25, 2012, 6 pages.
Decision of Rejection from State Intellectual Property Office of People's Republic of China, for Chinese Patent Application No. 201380021123.7, dated Aug. 6, 2018, 7 pages.

* cited by examiner

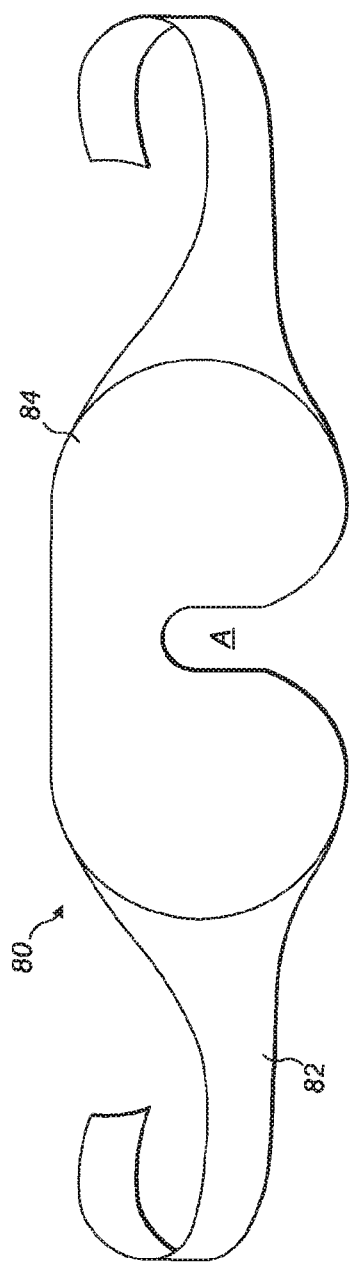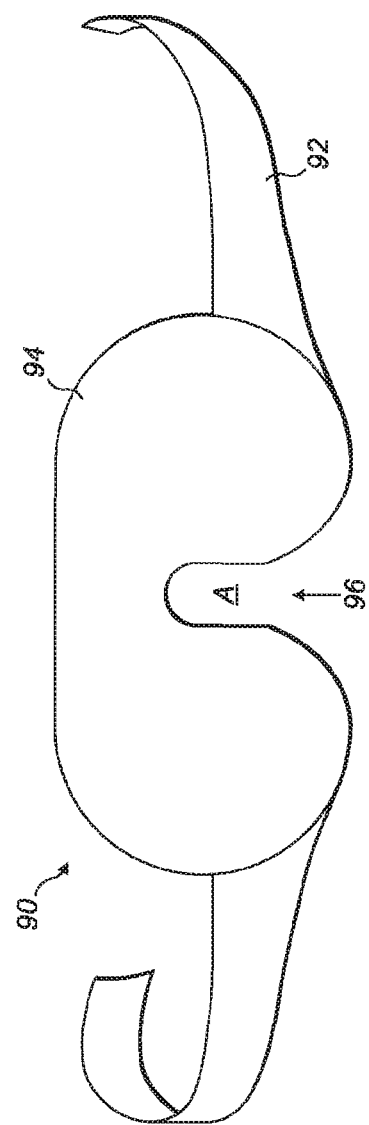

MEDICAL APPARATUS AND METHOD

CROSS REFERENCE TO RELATED APPLICATIONS

The present application is a continuation of U.S. patent application Ser. No. 14/380,255, filed Aug. 21, 2014, which is the U.S. National Stage of International Application No. PCT/GB2013/050254, filed Feb. 4, 2013, which in turn claims priority to United Kingdom Application No. GB1203005.2, filed Feb. 22, 2012.

The present invention relates to a medical apparatus and a method. In particular, but not exclusively, the present invention relates to a medical apparatus such as a facial mask, bandage or plaster for directing radiation into a patient's eyes or other area requiring treatment, and a method of operating such a medical apparatus.

Phototherapy has been used for various therapeutic and cosmetic purposes. It generally involves the use of specific wavelengths of light radiation being administered to a patient. Phototherapy may be used to treat chronic infections such as hepatitis (A, B or C), bacterial infections, wounds, precancer conditions, seasonal affective disorder (SAD), various dermatological and cosmetic purposes such as skin rejuvenation, and various eye diseases such as diabetic macular edema, retinopathy of prematurity, wet or dry age-related macular degeneration and diabetic retinopathy, for example.

Diabetic retinopathy is a condition in which damage to the retina in the eye occurs and is caused by diabetes. More specifically, diabetic retinopathy is the result of microvascular retinal changes where hyperglycemia-induced intramural pericyte death and thickening of the basement membrane cause damage to the wall of blood vessels in the eye. This damage changes the formation of the blood-retinal barrier and also makes the retinal blood vessels become more permeable. Small blood vessels, such as those in the eye, are particularly vulnerable to poor blood sugar control. An overaccumulation of glucose and/or fructose damages the blood vessels in the retina. Damaged blood vessels are likely to leak fluid and lipids onto the macula. This condition can therefore lead to impaired vision and ultimately blindness. The condition can be treated by preventing the complete dark adaptation of the eye by providing some degree of light radiation to the eyes or eyelids during sleep. This is because, during dark adaptation, the eye requires an increased oxygen level, and thus the blood vessels must work harder during dark adaptation.

Therefore by preventing complete dark adaptation of the eye, the blood vessels are less stressed and can rejuvenate over time. For diabetic retinopathy, preferably light having a wavelength of between around 460 to 550 nm is administered to the eyes or eyelids, which corresponds to the scotopic sensitivity of the eye. Of course for other diseases or conditions, other wavelength ranges may be useful.

It has been found useful to administer the radiation to the eye area by providing a mask type of device for a patient to wear during sleep, the mask configured to be secured over the patient's head to cover the eye area, and adapted to include light emitting sources in the region of the eyes. The light sources may be electroluminescent emitters, light emitting devices, light emitting cells (LECs), light emitting electrochemical cells (LEECs), LEDs or OLEDs, for example, and are arranged to emit light towards the eye area. The radiation acts to stimulate the rods of the eye leading to hyperpolarization and desensitization of the rod cells, which lowers their metabolic rates and hence results in a drop in oxygen consumption in the retina.

WO2011/135362 discloses a radiation treatment apparatus for directing electromagnetic radiation into a patient's eyes. Radiation treatment may be started or stopped by a patient input (on/off switch) to switch at least one organic semiconductor radiation emitting device on or off. Preferably the or each organic semiconductor radiation emitting device comprises an organic light emitting diode (OLED). Advantageously, the heat output from an OLED is less that that generated by a conventional light emitting diode (LED). OLEDs also emit light over a larger surface area than conventional LEDs, which assists in ensuring that radiation is directed correctly through the patient's eyelids and pupil to reach the retina of the eye. The or each OLED is mounted in a mask, goggles or a visor so that the electromagnetic radiation emitted by the or each OLED is directed into at least one eye of the patient, with the or each OLED in a predetermined position relative to the or each eye of the patient. Preferably, the mask, goggles or visor are provided with a securing strap or other means for securing the or each OLED to the patients face or head.

The radiation treatment apparatus disclosed WO2011/135362 may include a power supply and a controller for controlling the supply of power to the OLEDs. This provides the flexibility to vary the time and intensity of radiation exposure as part of a treatment regime. The duration and conditions of operation of the OLEDs may be recorded in a memory. In addition, sensor means may be provided to sense the surroundings of the apparatus, for instance to deactivate the OLEDs during daylight, or to take account of the body temperature or movement of the patient.

However, it is generally known that some patients do not adhere to the instructions of their doctor, physician or other advisor in terms of following the instructed treatment dosage and/or treatment regime, and/or follow the instructions on the patient information leaflet accompanying a medicine or apparatus.

In terms of a radiation treatment apparatus as described in WO2011/135362, the actual usage of the device by a patient in the correct manner (e.g. for the correct period of time and for the correct number of days, etc.), as prescribed by a doctor for example, cannot be guaranteed.

The present invention seeks to at least partly mitigate the above-mentioned problems.

According to a first aspect of the present invention there is provided a medical apparatus, comprising:
  a radiation source for emitting radiation towards an area to be treated of a patient;
  a mount element arranged to be worn by the patient for positioning the radiation source in a predetermined position relative to the area to be treated;
  a sensor element arranged to provide a signal indicative of whether the apparatus is being worn by the patient; and
  at least one controller arranged to receive the signal from the sensor, and to determine whether the apparatus is being worn by the patient, and to determine duration data indicative of the duration for which the radiation source emits radiation whilst the apparatus is being worn by the patient.

According to a second aspect of the present invention there is provided a method of operating a medical apparatus for emitting radiation towards an area to be treated of a patient, comprising:
  operating a sensor element to provide a signal indicative of whether the apparatus is being worn by a patient;

supplying the signal from the sensor element to a controller; and determining duration data indicative of the duration for which a radiation source emits radiation whilst the apparatus is being worn by the patient; using the signal from the sensor element.

Certain embodiments of the present invention provide the advantage that the apparatus can itself determine an indication of how long the apparatus has been used by the patient.

Certain embodiments of the present invention provide the advantage that a patient's usage of the apparatus can be recorded and/or transmitted for monitoring by a doctor or other monitoring service. Thus, compliance by the patient with a treatment regime can be determined. In some cases, a patient having knowledge that such compliance is being monitored will have a higher motivation to actually follow the treatment regime, thereby improving compliance with the instructed treatment regime.

Certain embodiments of the invention provide the advantage that data corresponding to a patient's usage of the apparatus can be stored, and/or transmitted continuously, intermittently or upon request to a receiver (such as a computer operated by the patient's doctor).

Embodiments of the invention are further described hereinafter with reference to the accompanying drawings, in which.

Figure 3:
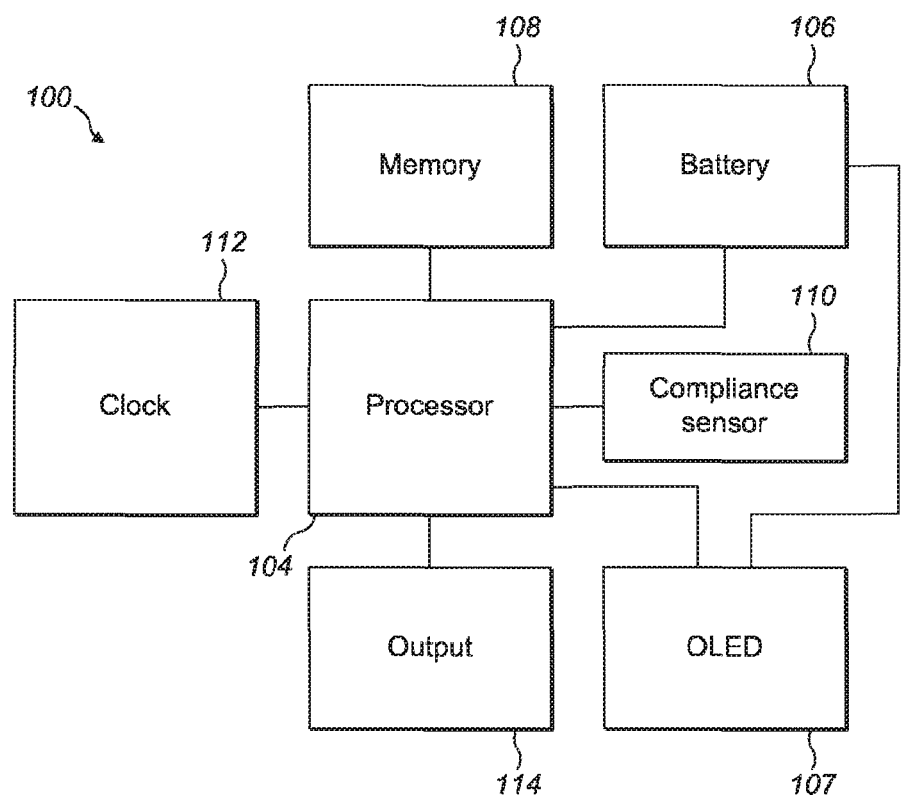
Figure 4:
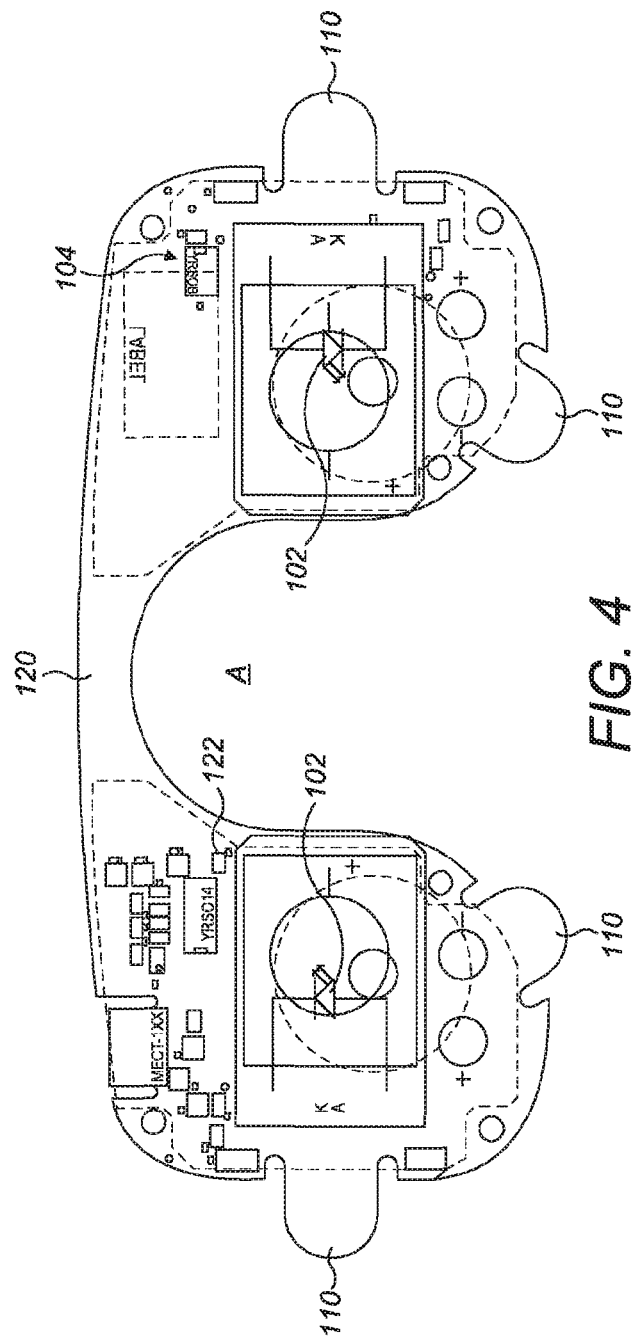
Figure 5:
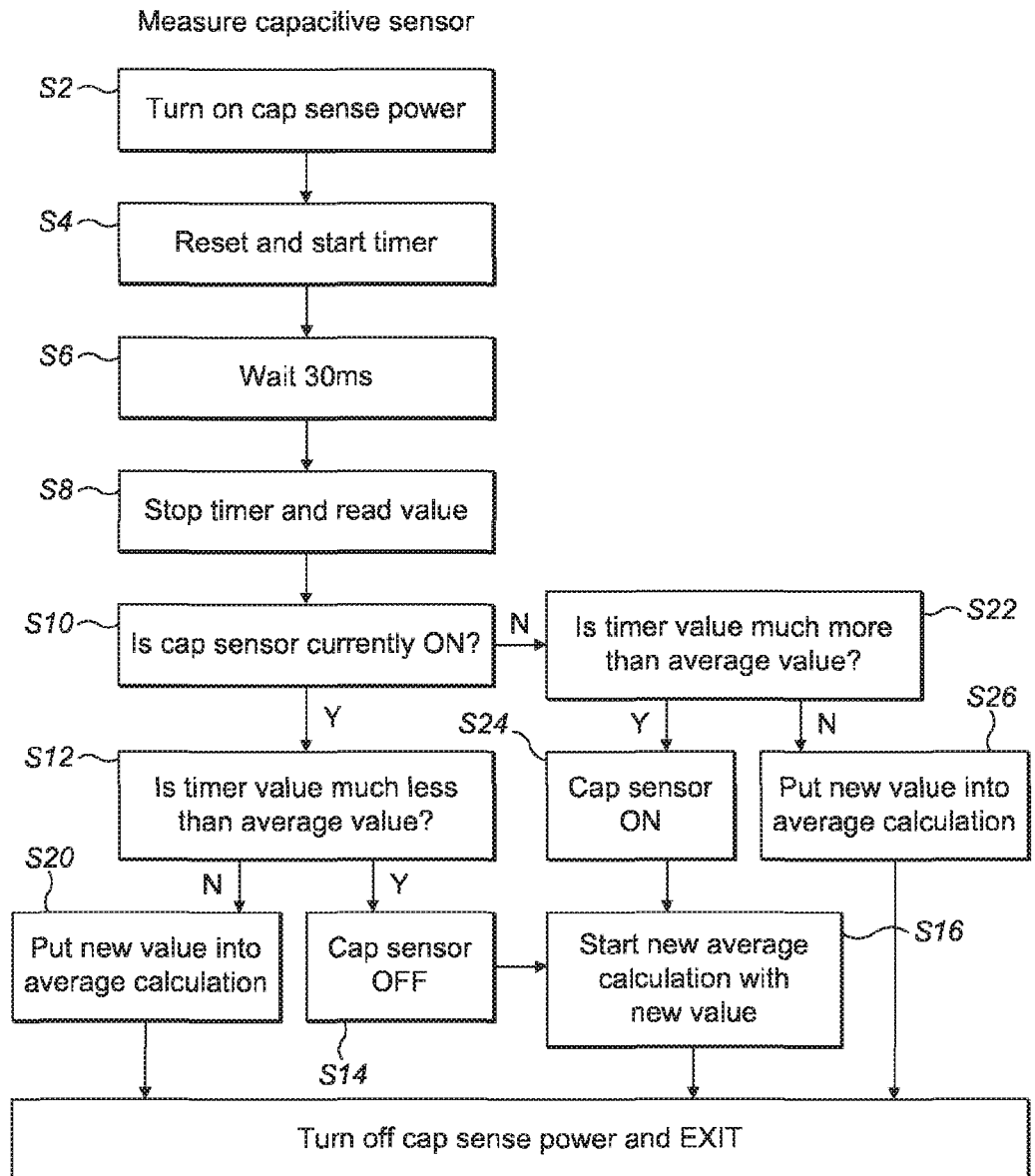
Figure 6:
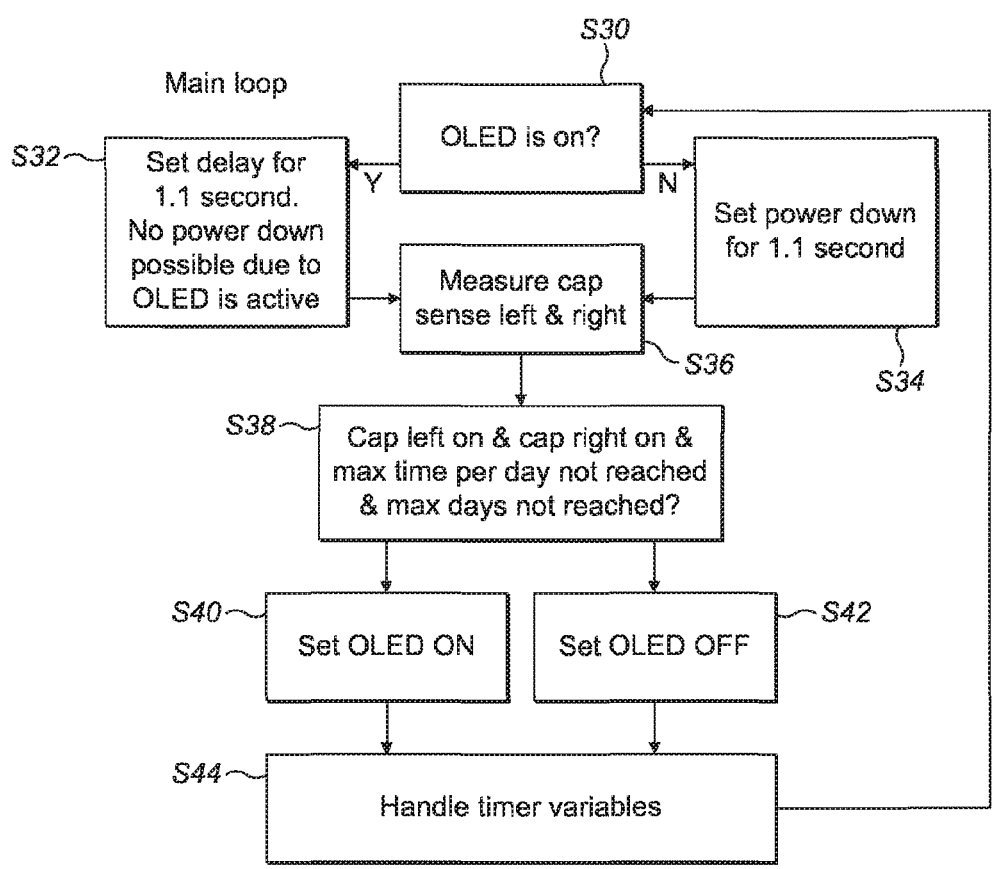
Figure 7A:
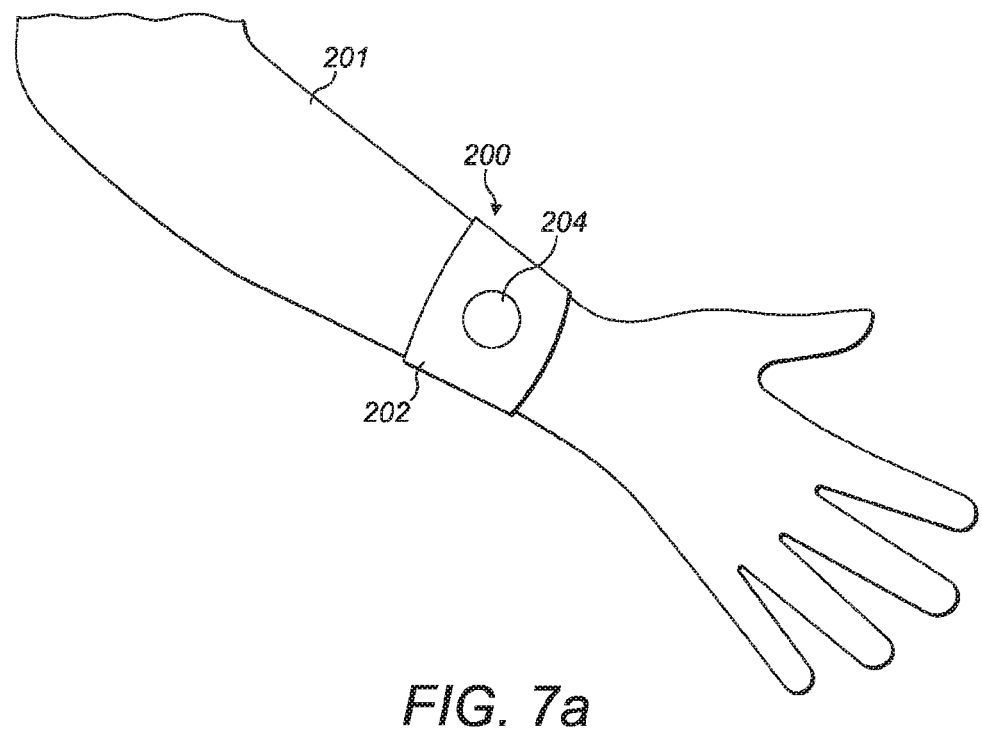
Figure 7B:
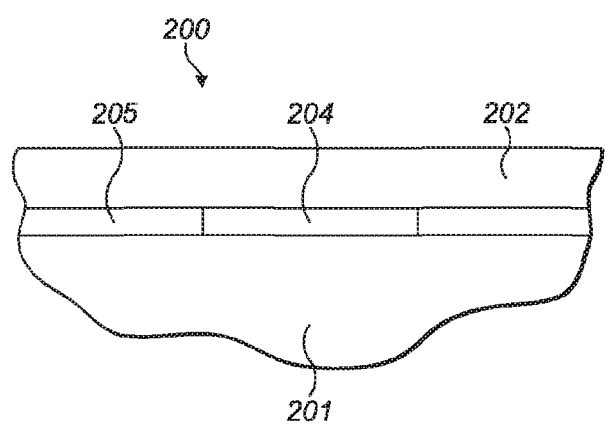

FIG. 3 schematically illustrates a radiation treatment apparatus according to an embodiment of the present invention;

FIG. 4 is a partially cut away view of a radiation treatment apparatus according to an embodiment of the present invention;

FIG. 5 is a flow chart describing how capacitive sensors are used within a radiation treatment apparatus according to an embodiment of the present invention;

FIG. 6 is a flow chart describing the operation of a radiation treatment apparatus according to an embodiment of the present invention;

FIGS. 7a and 7b illustrate an alternative radiation treatment apparatus;

FIG. 8 shows a face mask for a radiation treatment apparatus; and

FIG. 9 shows another configuration of a face mask for a radiation treatment apparatus.

In the drawings like reference numerals refer to like parts.

Certain elements of the apparatus described in WO2011/135362 may be used with the present invention. The contents of WO2011/135362 are incorporated herein by reference.

Figure 1:
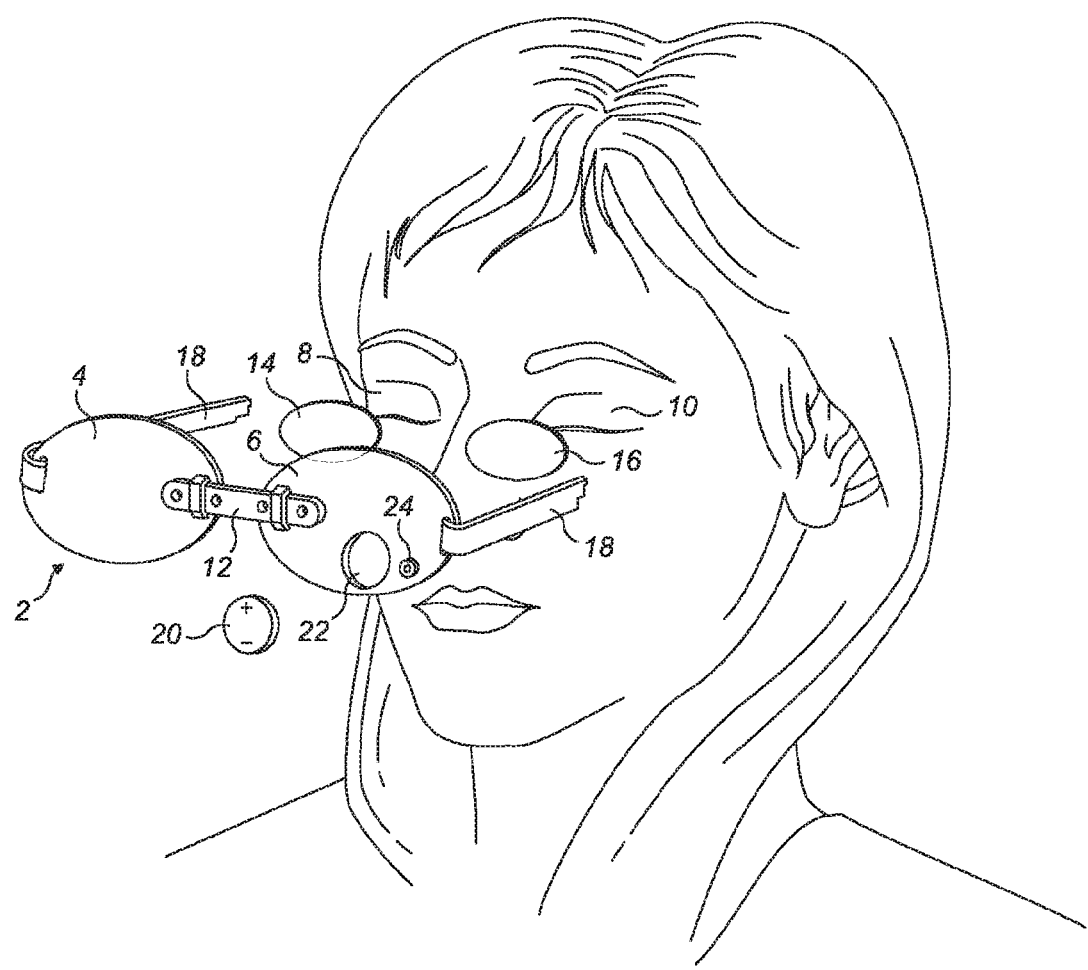
FIG. 1 illustrates an exploded perspective view of a radiation treatment apparatus.

As illustrated in FIG. 1, an exploded perspective view of a radiation treatment apparatus 2 as disclosed in WO2011/135362 comprises supports (or mounts) 4, 6 to be located adjacent to the eyes of a patient, the supports 4, 6 each supporting a respective OLED 14, 16. It will be appreciated that other radiation emitting devices could be used, though OLEDs are particularly advantageous for the reasons given above. It has been found that OLEDs emitting radiation within the range 460 nm to 550 nm, centred at 480 nm to 500 nm, are particularly suitable for treatment of diabetic retinopathy. This is because when the radiation is filtered through the eyelids 8, 10 of a patient who is asleep, radiation centred at about 510 nm reaches the retinas of the patient, which is particularly efficacious for the treatment of diabetic retinopathy. Alternatively, radiation centres at about 670 nm may be useful for the treatment of dry AMD, for example. Of course other ranges of wavelengths or light radiation are known to be useful to treat other conditions. It will also be appreciated that the dosage regime for light radiation will also likely include the time period for which radiation treatment occurs, the frequency of the periods, and luminance of the light radiation (measured by candela per metre squared—$cd/m^2$). Other conditions will of course require different dosage regimes. An adjustable strap 12 couples the supports 4, 6 together so that the spacing between the OLEDs 14, 16 can be matched to the spacing between a patient's eyes. A securing strap 18 secures the apparatus to the patients head. The OLEDs 14, 16 are powered by at least one battery 20 housed in at least one recess 22 and activated by a switch 24.

Figure 2:
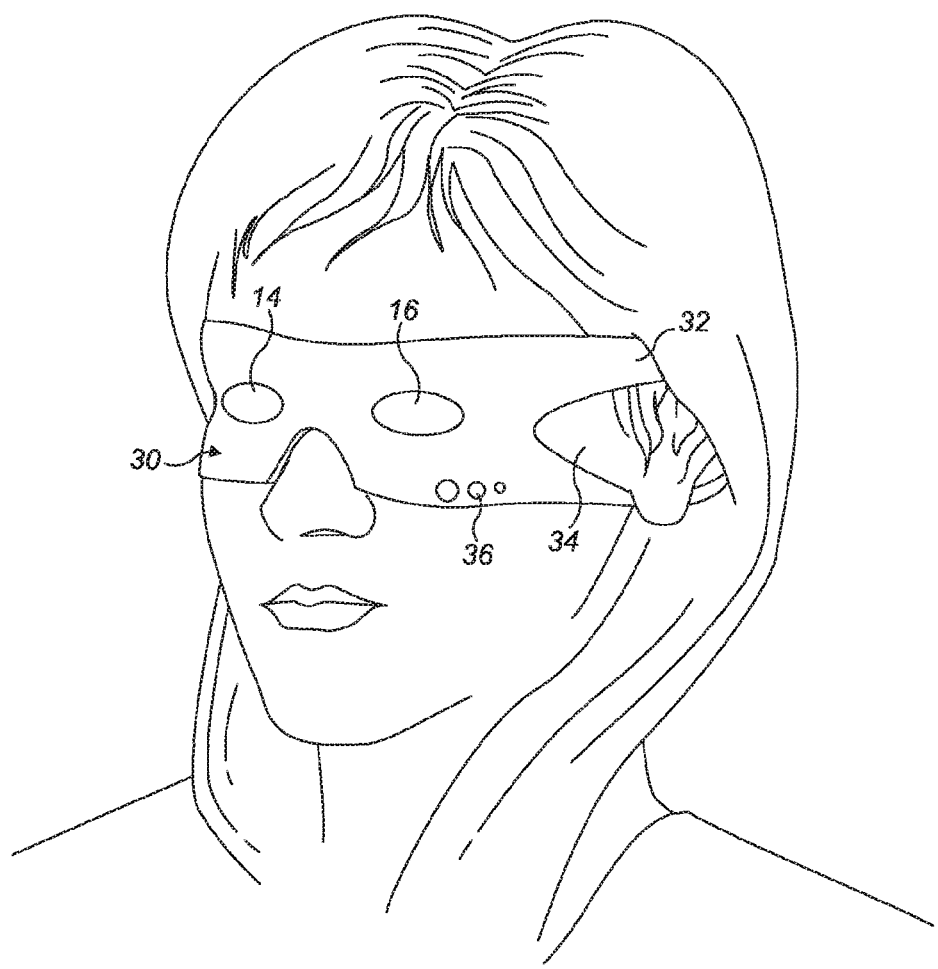
FIG. 2 illustrates an alternative radiation treatment apparatus.

WO2011/135362 discloses a range of alternative embodiments, for instance mounting the OLEDs in a face mask. The face mask may be formed from a flexible material. The face mask may be secured by a strap similar to strap 18 shown in FIG. 1, or it may, for instance, be adhesively mounted to the patient's eye socket or face. Alternatively, the OLEDs could be integrated into a visor mounted to the patient's head via a head strap. FIG. 2 illustrates an alternative radiation treatment apparatus disclosed in WO2011/135362 that takes the form of a mask. The mask comprises a flexible portion 30 to conform to the shape of the patient's face. The flexible portion 30 extends to form straps 32 which extend either around the patient's head or are secured by the patient's ears passing through apertures 34. The OLEDs 14, 16 are incorporated into the flexible mask such that they are brought into close proximity to the patient's eyes. FIG. 2 further illustrates one or more sensors 36, for instance to sense ambient light levels, body temperature or movement of the patient for use in controlling the operation of the apparatus to minimise disturbance to the user's sleep.

The present invention provides a radiation treatment apparatus comprising an improvement to the radiation treatment apparatuses disclosed in WO2011/135362. As noted above, some patients may not correctly follow a treatment regime prescribed by a doctor. Specifically, some patients may not correctly wear the apparatus or may not wear the apparatus at all, for instance removing the apparatus before the full prescribed radiation exposure has been reached for that treatment session. The present invention allows compliance with a treatment regime to be monitored by detecting when or for how long the apparatus is worn. This allows a determination to be made whether the correct radiation exposure has been delivered to the patient.

Referring now to FIG. 3, this schematically illustrates components of an apparatus 100 in accordance with an embodiment of the present invention. It will be appreciated that the purpose of FIG. 3 is to present the main functional units of an apparatus in accordance with an embodiment of the present invention, and places no limitation on the actual structure of the apparatus. However, one such structure would be a structure as depicted in FIG. 1 or FIG. 2, for example. The apparatus 100 comprises at least one radiation source 102, for instance at least one electroluminescent emitter, in this case an OLED. The radiation source 102 or each radiation source may be positioned in or on a mask, goggles or visor, or other such support structure or mount so as to be placed in a predetermined position relative to a patient's eye (or other area to be treated). The support structure may be for example as generally shown in FIGS. 1 and 2 and as described in WO2011/135362, and so will not be further described here. The apparatus further comprises a processor 104 and a battery 106 (or other source of power, for instance a power supply socket allowing a power supply wire to be coupled to the apparatus 100). The battery 106 is coupled to the processor 104 and the radiation source 102 so as to enable the supply of power to both. The processor 104 is coupled to the radiation source 102 so as to control the operation of the radiation source, and in particular to turn the radiation source 102 on and off in accordance with a prescribed treatment regime. The apparatus further comprises a memory 108 coupled to the processor 104. The memory 108 is arranged to store instructions for controlling the processor 104 and data relating to the treatment regime, for instance intensity of electromagnetic radiation emitted by the radiation source 102.

FIG. 3 further illustrates a compliance sensor 110 coupled to the processor 104. The compliance sensor is arranged to provide a signal to the processor 104 indicative of whether the apparatus 100 is being worn by the patient. In one embodiment, to be described in greater detail below, the compliance sensor 110 comprises a capacitive sensor arranged to provide a signal to the processor 104 indicative of the capacitance at the sensor, which can be interpreted to determine whether the sensor is close to or in contact with skin (indicating that the apparatus 100 is being worn) or whether the sensor is close to or in contact with air (indicating that the apparatus 100 is not being worn). FIG. 3 further illustrates a clock circuit 112 coupled to the processor 104. The clock circuit 112 is arranged to provide a timing signal allowing the processor 104 to calculate the duration for which the apparatus 100 has been worn, or the times at which the apparatus is put on or taken off, or both. Data relating to when and/or for how long the apparatus has been worn (hereinafter compliance data) may be stored in memory 108. Alternatively, or in addition, the compliance data may be passed from the processor 104 to an output circuit 114 for transmission to another device. For instance, the output circuit may be a radio frequency (RF) transmitter arranged to transmit compliance data wirelessly to a patient's computer, or directly or indirectly to a doctor's computer to allow compliance of the patient with a treatment regime to be monitored. Alternatively, the output 114 could be used to download compliance data periodically from the memory, for instance when the patient visits the doctor.

In addition to passively recording when and/or for how long the patient has worn the apparatus, the signal from the compliance sensor 110 may be used to assist the processor 104 in controlling the radiation source. This may be to ensure that the radiation source 102 is only activated when the apparatus 100 is being worn. Additionally, the processor 104 may be adapted to monitor the duration of radiation exposure while the apparatus 100 is being worn such that further exposure is prevented, i.e. the radiation source is switched off, once the prescribed dosage for that dosage session has been reached. Data relating to the duration of use, that is data recording the patient's radiation exposure from the OLED whilst wearing the mask may form part of the compliance data. By monitoring when the apparatus is worn, embodiments of the present invention provide an apparatus capable of autonomously delivering a specific radiation dosage according to a predetermined treatment regime to the eye, or eyes, or other area of a patient. Embodiments of the present invention further provide the ability to make records of, and monitor, compliance with a predetermined treatment regime.

A capacitive sensor, such as may be used to form the compliance sensor 110, is operated by taking a first measurement of the capacitance of the sensor at a first time and at a second, later, time taking a second measurement of the capacitance of the sensor. When a capacitive sensor is exposed to air the capacitance varies significantly due to natural variations in the surroundings of the sensor. Conversely, when a capacitive sensor is in contact with, or in close proximity to, a patient's skin the capacitance remains more stable. Consequently, if the first and second measurements of the capacitance of the sensor are close to one another (within a predetermined tolerance) then this indicates that the sensor is in contact with or close to the patient's skin (and hence indicates that the apparatus is being worn). If the two measurements are further apart than the predetermined tolerance, then this indicates that the apparatus is not being worn. In one embodiment a capacitive sensor periodically charges and discharges at a frequency determined by its capacitance (which, as noted above varies according to the surroundings of the sensor). The capacitive sensor may transmit this periodic signal to the processor 104. By comparison to a regular timing signal received from the clock 112, the frequency of the signal from the sensor can be determined and compared with earlier readings to determine whether the apparatus is being worn.

Alternatives to capacitive sensors to form the compliance sensor 110 include thermal sensors, ultrasonic sensors, photodiodes, a strain gauge that is for example coupled to an apparatus securing strap (to measure strain as the strap is stretched when pulling on the apparatus) or coupled to another portion of the apparatus and capable of measuring bending as the apparatus is put on, and a blood oxygen monitor. Indeed, any sensor known in the art capable of providing an indication whether the apparatus is being worn may be used. Where a capacitive sensor, in particular, is used it can be desirable to use multiple capacitive sensors such as two sensors, one on either side of a mask, three sensors, or four sensors spaced apart around a mask to accommodate variations in the shape of patient's faces. For instance, for some patients not all of the sensors may contact the patient's face. There are surprisingly large variations in facial shapes due to genetics and origin. In some embodiments it may be sufficient for one capacitive sensor to register that it is in contact with, or in close proximity to, the patient's skin to determine that the apparatus is being correctly worn. Alternatively, it may be necessary that every sensor, or a predetermined number of sensors, register that they are in contact with, or in close proximity to, the patient's skin to determine that the apparatus is being correctly worn. The higher number of sensors may help to obtain a more reliable result.

As noted above, compliance data may be stored within the apparatus 100 in memory 108, or compliance data may be transmitted from the apparatus 100 continuously or intermittently, or both. The method of sending data, e.g. compliance data, to a device (for example a computer), may be known as machine-to-machine monitoring (M2M). In a first exemplary embodiment, the output circuit 114 may be an RFID chip such that compliance data stored in memory 108 may be retrieved wirelessly from the apparatus periodically, for instance when the patient visits their doctor. The apparatus may optionally include a recharging element using an induction to power the RFID chip by induction (rather than using battery 106).

In a second exemplary embodiment, output circuit 114 may comprise a Bluetooth® transmitter arranged to transmit compliance data to an associated device such as a mobile telephone or a computer, where that data may be stored or further transmitted, for instance ultimately to a doctor or other person responsible for monitoring the patient's compliance with the treatment regime. It will be appreciated that further variations are possible, for instance using a wired connection to the apparatus. Wired connections may, for example, be via USB, FireWire™, Thunderbolt™ or Lightning™. Alternatively, data may be communicated via "Li-Fi" (the transmission of communication using visible light).

An application (or 'app') specifically created to interact with the mask may be installed on a mobile telephone (cellular phone), which may be programmed to store information relating to the use of the mask. For example, the application may be configured to log mask wear history (e.g. including total duration of wear and specific times of wear) and/or set reminders to tell the patient when they need to wear the mask. The application may also further transmit data to a doctor or other person responsible for monitoring the patient's compliance with the treatment regime. It will be appreciated that software of similar capabilities may provide the same function when installed on any PC, tablet or other suitable electronic device. The data from the mask may be transmitted to the application and/or the software (installed on any suitable electronic device) via any wireless or wired means.

M2M monitoring may use short range wireless communication (for example in homes and hospitals) which may be via personal area networks (e.g. Bluetooth™, Zigbee™, MyWi™) or local area networks (e.g. Wi-Fi).

Telehealth refers to the delivery of health-related services and/or information via telecommunication technologies (and it is appreciated that this may be known by other names elsewhere). Telecare is a similar system in which a patient is connected with a monitoring centre through which an alarm is raised if the patient requires assistance. The mask of the present invention may be integrated with such systems to monitor health and/or transmit data to any required locations. For example, for long range monitoring (e.g. from a home to a doctor in a different location), these systems may be utilized to provide communication via the internet.

Referring now to FIG. 4, there is shown a partially cut away view of a radiation treatment apparatus according to an embodiment of the present invention. Specifically, FIG. 4 illustrates a printed circuit board (PCB) 120 supporting the OLEDs 102 (for an apparatus having two OLEDs, one for each eye) and shaped to fit on or in an eye mask generally of the form illustrated in FIG. 2, 8 or 9. The area A indicates generally where the user's nose may be when the mask is fitted to the user's face. FIG. 4 shows a processor 104 and four separate capacitive sensors 110, forming compliance sensors, spaced apart around the periphery of the PCB 120. The capacitive sensors extend from the PCB as flaps that may be folded against a user's face. There is also shown a power supply transistor chip 122 for controlling the supply of power to the OLEDs and the processor 104.

In the embodiment shown in FIG. 4 there is a single processor 104, which additionally implements the functions of the clock 112, memory 108 and output 114 shown in FIG. 3. It will be appreciated that the PCB shown in FIG. 4 may, as a whole, be considered as a mount for positioning the various elements with respect to the user. The PCB can be incorporated into the design of a mask as in FIG. 2, within the mask structure or adhered onto a mask structure. Therefore the mask structure itself may be considered the mount. Forming the main electronic components onto a PCB structure may help enable a simpler, more cost effective manufacturing process. Of course it will be realised that the PCB or mount may be of any suitable shape to fit together with any suitable facial mask. The PCB or mount may have a different layout and design when used in a bandage or plaster, for example.

Referring now to FIG. 5, this illustrates in the form of a flow chart the process of determining whether the patient is wearing the apparatus 100 by interpreting the output from a capacitive compliance sensor 110 in a processor 104. At step S2 the processor 104 switches on a small current to the capacitive sensor 110, the current being supplied to a processor pin coupled to one terminal of the capacitive sensor 110. At step S4 a timer controlled by the clock circuit 112 is reset and started. At step S6 the processor waits 30 mS (milliseconds) while counting the number of oscillations of the voltage charging and discharging across the capacitive sensor. At step S8 the timer is stopped once 30 mS is reached and the number of oscillations is read. At step S10 a check is made whether the capacitive sensor is turned on. That is, a check is made whether the previous readings from the capacitive sensor indicate that the apparatus is being worn. If the capacitive sensor is ON this indicates that the previous recorded state of the sensor is that the apparatus is not being worn (the sensor is not in contact with skin. If the capacitive sensor is on then at step S12 a check is made whether the number of oscillations counted in the 30 mS period of time is significantly lower than the average of previous measurements. When a capacitive sensor is in contact with, or in close proximity to, skin the capacitive load is increased, which lowers the number of oscillations. The processor checks to see whether the oscillation count is lower than the average by a predetermined proportion or amount. If the answer is yes then this indicates that the patient has put the apparatus on, thereby bringing the sensor into contact with skin. Therefore at step S14 the status of the sensor is set to OFF. This change of state may be used to update information held in the memory 108 or sent to the output 114 indicating when and/or for how long the patient has worn the apparatus. Given the change of state, at step S16 the running average is reset and a new average calculation begun with the new reading. At step S18 the power supply to the capacitive sensor is turned off to conserve power. In order to conserve power the compliance monitoring functions may be set to only operate periodically, for instance once per second, such that for the majority of the time the apparatus is in a reduced power mode. If at step S12 it is determined that the count of oscillations is not significantly less than the average value (or is the same, or higher) it is determined that the patient continues to not be wearing the apparatus. At step S20 the average number of oscillations in a 30 mS period is updated. That is, the average of a predetermined number of previous measurements is updated with the new measurement allowing the sensor to keep track of gradually changing capacitive conditions. The process then returns to step S18.

Similarly, if at step S10 it is determined that the current states of the sensor is OFF (indicating that the patient was wearing the apparatus when the sensor was last checked) then at step S22 a check is made whether the number of oscillations counted in the 30 mS period of time is significantly higher than the average of previous measurements. If the answer is yes then this indicates that the patient has removed the apparatus. Therefore at step S24 the status of the sensor is set to ON. At step S16 the running average is reset and a new average calculation begun with the new reading and at step S18 the power supply to the capacitive sensor is turned off to conserve power. If at step S22 it is determined that the count of oscillations is not significantly higher than the average value (or is the same, or lower) it is determined that the patient continues to be wearing the apparatus. At step S26 the average number of oscillations in a 30 mS period is updated and the process returns to step S18.

Referring now to FIG. 6, this illustrates in the form of a flow chart the main processing loop of a radiation treatment apparatus according to an embodiment of the present invention. The flow chart in FIG. 6 operates as a continuous loop until the power supply is lost, as is the case for the flow chart of FIG. 5. Similar to FIG. 5, the operation of FIG. 6 is designed to conserve power by powering down approximately once per second and by using a lower power and relatively slow 32 kHz clock. Upon powering up each cycle the processor is arranged to read the capacitive sensors as described in FIG. 5, update the stored compliance data (or transmit new compliance data) and then power down again.

At step S30 the processor checks if the OLED or each OLED is currently on. If the OLEDs are on then the apparatus cannot be powered down, so at step S32 the processor waits 1.1 S. If power down is possible (i.e. the OLED is not switched on) then at step S34 the processor powers down for 1.1 S before turning on and measuring the or each capacitive sensors at step S36. At step S38 the processor determines whether at least one sensor on the left of the apparatus mask and at least one sensor on the right are indicating that the apparatus is being worn. The processor also determines if further radiation emissions are necessary to meet the prescribed radiation emission for that dosage session. If the answer to both questions is yes then at step S40 the or each OLED is switched on or remains on. If the answer to at least one question is no then at step S42 the or each OLED is switched off. At step S44 the process updates the timers recording the duration and/or times at which the mask was worn and/or radiation was emitted while the mask was worn. The process then returns to step S30.

A further embodiment of the present invention is shown in FIGS. 7a and 7b. Apparatus 200 incorporates the general principles of the embodiments described above, but is arranged to be worn as a bandage over any area of a user as required. Here the apparatus is used on the arm 201 of a patient. The bandage may be tied or adhered to the arm 201 in a known manner. As shown in the cross-sectional view of FIG. 7b, the apparatus 200 includes a flexible outer layer 202, which may be soft cotton for example for patient comfort. The apparatus 200 also includes a radiation source 204, which in this example is an OLED, on the skin-facing side of the apparatus in use. The radiation source is linked to a controller (not shown) which may function in the same way as the processor 104 described above. In turn, the controller is also linked to a compliance sensor for monitoring the usage of the apparatus 200, in a similar manner as described above. For ease, the OLED 204, controller and sensor may be formed on a PCB 205 that can effectively be laminated onto the outer layer 202. Compliance can be monitored in the same way with respect to FIGS. 5 and 6. Optionally, a further inner layer may be included to help improve patient comfort. Aptly this layer would be transparent at least in the area of the OLED so as to not interfere with the radiation emission.

Various modifications to the detailed designs as described above are possible. For example at least some of the separate functional components illustrated in FIG. 3 may be reduced in number by combining their functions into a single processor. The skilled person will appreciate that the present invention may be implemented in hardware or software as required.

Although the radiation source has been described above as an OLED, this may be any electroluminescent emitter, light emitting device, light emitting cell (LEC), light emitting electrochemical cell (LEEC), LED or similar device.

Although discrete, intermittent measurements have been described above, it will be realised that continuous monitoring of radiation emission or wear by the user may be possible.

The apparatus of the present invention when embodied as a facial mask may take the general form as shown in FIG. 1 or FIG. 2, or other similar form to appropriately locate the radiation source in the eye region and encompass the above-described features of the invention. FIG. 8 shows another configuration of a facial mask 80 having a strap or straps 82 and a facial portion 84 for holding the components of the invention described above. FIG. 9 shows a yet further configuration of a facial mask 90 having a strap or straps 92 and a facial portion 94. The strap(s) 92 connect with the facial portion 94 at a lower position on the portion 94 (in the orientation shown on the drawing and in normal use) compared with the mask 80. By lowering the relative position of the strap(s) 92, the strap(s) is provided closer to an opening 96 to the area A where a user's nose may be located in use. As such, upon positioning the mask 90 on the head, the tension of the strap(s) 92 acts to increase the width of the opening 96. This may be useful for users with larger than average noses and/or heads.

As an optional additional feature, the apparatus of the present invention may include one or more moisture detector for detecting the presence of liquid on the apparatus. An internal moisture detector may be used to determine whether a user has exposed the apparatus to a wet environment, for example dropping the apparatus in a drink or bath tub, thereby helping to identify the liability for damage to the apparatus.

As an alternative to the above-described arrangement, a medical apparatus may be provided in which an additional sensor is provided, such as a capacitance sensor, as a user input control on the apparatus. The capacitance sensor may be in the form of a button that a user presses to initiate start-up of the apparatus. Then, within a predetermined time length such as 10 seconds from pushing the button, the user should put the apparatus in place on the area to be treated (as confirmed by the other capacitance sensors 110). By incorporating such a user-operated sensor, the apparatus then requires a deliberate act by the user to switch on the apparatus prior to the monitoring. This may help positively confirm when the device should be turned on to emit radiation (i.e. an extra check), and may also help positively reinforce to the user the need to comply with the specified treatment regime.

In another alternative arrangement, the sensor element of the apparatus may be in the form of a light emitter and receiver arrangement, for example including an infrared light emitter at one location of the apparatus and a photo-detector or diode located at another location of the apparatus. Aptly, the emitter and receiver may be respectively located on either side of a nose locating area of a facial mask, such that by placement of the mask on a user's face, the user's nose will block any infrared light from the emitter being received at the receiver. That is, the "line of sight" of the infrared radiation is blocked by the nose when the mask is being worn. Thereby, the receiver will be able to provide an indication (e.g. a signal) to monitor whether the mask is in place on the user's face, and optionally also for how long the mask is in place on the user's face by providing a signal to a controller in a similar manner as described above. Such an arrangement may be used instead of the compliance sensor 110 described above, or may be used as an addition to one or more compliance sensor, such as the capacitance sensor described above. Provision of such an arrangement may help to prevent a user purposely or inadvertently 'cheating the system', for example where a facial mask is worn or rides up above the eye area but is still in contact with the skin.

In addition to the above-described functions, apparatus according to the invention may also be programmed with a specified, predetermined dosage regime, e.g. treatment time length and number of treatments (e.g. 8 hours treatment for 10 days), and light intensity/luminance level. Aptly the intensity may be variable, for instance at a less bright level at the beginning of a treatment period (as the user gets used to the apparatus or begins to fall asleep) and increases to a further brightness level for a next part of the treatment period.

In a further variation, the apparatus of the invention may be designed to receive instructions on a dosage regime that may be set by a doctor or other instructor. The steps for receiving instructions may be opposite to the above-described sending of information from the apparatus. For example, a RF receiver may be included that receives an input and sends the signal to processor 104. The processor may then control the radiation source 107 in accordance with the instructions. This may be useful if the dosage regime for a patient needs to be changed over time, for example as their health improves.

With the above-described invention, a dosage scheme of radiation can be automatically delivered to a patient when the apparatus is secured in place on the patient. By monitoring when and for how long the patient wears the apparatus it can be monitored whether the full dosage scheme is delivered to the patient: that is, the patient's compliance with the dosage scheme can be monitored.

It will be clear to a person skilled in the art that features described in relation to any of the embodiments described above can be applicable interchangeably between the different embodiments. The embodiments described above are examples to illustrate various features of the invention.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A medical apparatus, comprising:
   a radiation source for emitting radiation towards at least one eye of a patient;
   a mount element comprising a mask arranged to be attached to the patient's face for positioning the radiation source in a predetermined position in the region of the at least one eye of the patient so that, in use, the radiation source emits radiation towards the at least one eye of the patient, wherein the mask comprises a flexible portion to conform to the shape of the patient's face;
   a sensor element arranged to provide a signal indicative of whether the apparatus is being worn by the patient;
   at least one controller arranged to receive the signal from the sensor, and to determine whether the apparatus is being worn by the patient, and to determine duration data indicative of the duration for which the radiation source emits radiation whilst the apparatus is being worn by the patient; and
   wherein the sensor element forms a flap extending from a periphery of the mount element.

2. A medical apparatus as claimed in claim 1, wherein the controller is further arranged to control the operation of the radiation source.

3. A medical apparatus as claimed in claim 2 wherein the controller is arranged to control the operation of the radiation source such that radiation is emitted when the signal received from the sensor element indicates that the apparatus is being worn by the patient.

4. A medical apparatus according to claim 1, wherein the radiation source comprises an organic light emitting diode (OLED).

5. A medical apparatus according to claim 4, wherein:
   the radiation source comprises a pair of OLEDs supported by the mount element such that when the apparatus is used by a patient each OLED is in a predetermined position relative to at least one eye of the patient.

6. A medical apparatus as claimed in claim 1, further comprising at least one further sensor element arranged to provide a signal indicative of whether the apparatus is being worn by the patient.

7. A medical apparatus according to claim 1, wherein the sensor element comprises a capacitive sensor supported by the mount such that when the apparatus is worn by a patient the capacitive sensor is in close proximity to the patient's skin.

8. A medical apparatus according to claim 1, wherein the sensor element comprises a light emitter and receiver arrangement supported by the mount such that when the apparatus is worn by a patient the receiver is prevented from receiving light from the light emitter.

9. A medical apparatus according to claim 1, wherein the controller is arranged to control the radiation source such that radiation is emitted when the signal received from the sensor element indicates that the apparatus is being worn by the patient only if a predetermined radiation emission dosage has not been exceeded.

10. A medical apparatus according to claim 1, further comprising a memory component arranged to store the duration data.

11. A medical apparatus according to claim 1, further comprising an output circuit arranged to transmit the duration data.

12. A medical apparatus according to claim 11, wherein the output circuit comprises an RFID circuit arranged to transmit the duration data to an associated RFID receiver.

13. A medical apparatus according to claim 1, wherein the sensor element comprises a user-operated sensor.

14. The medical apparatus of claim 1, wherein the sensor element comprises a plurality of sensor elements spaced apart from each other around a periphery of the mount element.

15. The medical apparatus of claim 1, wherein the flap can be folded against the patient's face.

16. The medical apparatus of claim 1, wherein the sensor element comprises a plurality of sensor elements forming flaps at spaced apart locations along the periphery of the mount element.

17. A medical apparatus, comprising:
- a radiation source for emitting radiation towards at least one eye of a patient;
- a mount element, wherein the mount element is shaped to fit together with a mask arranged to be attached to the patient's face for positioning the radiation source in a predetermined position in the region of the at least one eye of the patient so that, in use, the radiation source emits radiation towards the at least one eye of the patient, wherein the mask comprises a flexible portion to conform to the shape of the patient's face;
- a sensor element arranged to provide a signal indicative of whether the apparatus is being worn by the patient;
- at least one controller arranged to receive the signal from the sensor, and to determine whether the apparatus is being worn by the patient, and to determine duration data indicative of the duration for which the radiation source emits radiation whilst the apparatus is being worn by the patient and
- wherein the sensor element forms a flap extending from a periphery of the mount element.

\* \* \* \* \*